United States Patent
Abanto et al.

(10) Patent No.: US 7,203,970 B2
(45) Date of Patent: Apr. 17, 2007

(54) BODY ARMREST ASSEMBLY

(76) Inventors: Edward A. Abanto, 191 Larch Ave., Dumont, NJ (US) 07628; Power Abanto, 101 W. Central Ave., Bergenfield, NJ (US) 07621

( * ) Notice: Subject to any disclaimer, the term of this patent is extended or adjusted under 35 U.S.C. 154(b) by 162 days.

(21) Appl. No.: 11/119,164

(22) Filed: May 2, 2005

(65) Prior Publication Data

US 2006/0162038 A1    Jul. 27, 2006

Related U.S. Application Data

(60) Provisional application No. 60/647,376, filed on Jan. 26, 2005.

(51) Int. Cl.
*A41D 13/08* (2006.01)
*F41A 9/62* (2006.01)

(52) U.S. Cl. ................................ 2/16; 42/94

(58) Field of Classification Search .................. 2/16, 2/69, 456, 114, 59, 115, 93, 94, 44, 338; 128/878, 128/882; 42/94, 106; 602/4, 5, 62, 19, 20, 602/21, 61; 224/197, 270, 646, 647, 913
See application file for complete search history.

(56) References Cited

U.S. PATENT DOCUMENTS

| | | | | |
|---|---|---|---|---|
| 5,111,983 A | * | 5/1992 | Simmons et al. | 224/258 |
| 5,385,536 A | * | 1/1995 | Burkhead et al. | 602/20 |
| 5,819,461 A | * | 10/1998 | Killian | 42/94 |
| 6,336,576 B1 | * | 1/2002 | Easter | 224/153 |
| 6,789,344 B2 | * | 9/2004 | Cain | 42/94 |
| 6,893,098 B2 | * | 5/2005 | Kohani | 297/468 |

* cited by examiner

*Primary Examiner*—Tejash Patel
(74) *Attorney, Agent, or Firm*—Clifford G. Frayne

(57) ABSTRACT

A body armrest for relieving spinal, back or neck pain, and for providing a three point support for the upper torso combining the spine with a right and left body armrest, the body armrest constructed having a centrally disposed sleeve for the insertable receipt of a waist belt, the centrally disposed sleeve having an upper cradle or platform section extending generally horizontally outwardly therefrom, the cradle or platform section for contact with the individuals elbow and forearm, the sleeve member having depending therefrom, an arcuate contoured leg, the arcuate contoured leg contoured to the arcuate contour of the hip as it extends outwardly from the waist, both the cradle or contoured depending leg may be hingeably secured to the centrally disposed sleeve.

12 Claims, 4 Drawing Sheets

BODY ARMREST ASSEMBLY

RELATED APPLICATIONS

Applicant claims the benefit of provisional application Ser. No. 60/647,376, filed Jan. 26, 2005.

BACKGROUND OF THE INVENTION

1. Field of the Invention

The present invention relates to an orthopedic device and more particularly to a pair of armrests which would be worn about the waist of an individual and supported by a waist belt and the hips of the individual allowing the forearms of the individual to rest on the device thereby distributing upper body weight to the device and not solely to the spine.

2. Description of the Prior Art

Many individuals suffer from back pain, either intermittent or continuous. The pain is usually associated with the individual's spine or the muscle fabric supporting the upper torso. Various drugs can be utilized to help alleviate the pain, but in most instances, the individual whether suffering continuous or intermittent back pain is forced to utilize and wear some form of back support, body brace, sling, or neck traction or even crutches in order to provide support for the upper torso and to transfer some of the weight away from the spine.

Applicant's device provides an armrest in the form of a platform or cradle support which allows an individual suffering from the aforesaid maladies to rest his elbows and forearms on the platform device and thereby having a three point contact for support of the upper torso, the spine, and the elbow and forearms of the individual.

OBJECTS OF THE INVENTION

An object of the invention is to provide a novel body armrest which can be worn by the individual about the waist and which allows the individual to support the elbows and forearms on the body armrest thereby providing three point distribution of the upper body weight and to further transfer upper body weight to the hips.

Another object of the present invention is to provide for a novel body armrest in which the armrest can be positioned and worn about the waist utilizing a belt.

A still further object of the present invention is to provide for a novel body arm rest which has an arcuate lower leg which is contoured to the hips of the individual.

A still further object of the present invention is to provide for a novel body armrest in which the platform or cradle portion of the armrest is cushioned.

A still further object of the present invention is to provide for a novel body armrest in which the cradle armrest are fashioned about the body by a belt, supported by the contoured hip and provide a cradle or platform for each elbow and forearm of the individual.

A still further object of the present invention is to provide for a novel body armrest in which the cradle or platform is hingeable.

A still further object of the present invention is to provide for a novel body armrest in which the arcuate lower portion engaging the hip is hingeable.

A still further object of the present invention is to provide for a novel body armrest which incorporates an arm strap cooperable with the arm rest to restrain the forearm.

SUMMARY OF THE INVENTION

A body armrest for relieving spinal, back or neck pain, and for providing a three point support for the upper torso combining the spine with a right and left body armrest, the body armrest constructed having a centrally disposed sleeve for the insertable receipt of a waist belt, the centrally disposed sleeve having an upper cradle or platform section extending generally horizontally outwardly therefrom, the cradle or platform section for contact with the individuals elbow and forearm, the sleeve member having depending therefrom, an arcuate contoured leg, the arcuate contoured leg contoured to the arcuate contour of the hip as it extends outwardly from the waist, both the cradle or contoured depending leg may be hingeably secured to the centrally disposed sleeve.

BRIEF DESCRIPTION OF THE DRAWINGS

These and other objects of the present invention will become apparent, particularly when taken in light of the following illustrations wherein.

DETAILED DESCRIPTION OF THE INVENTION

Figure 1:
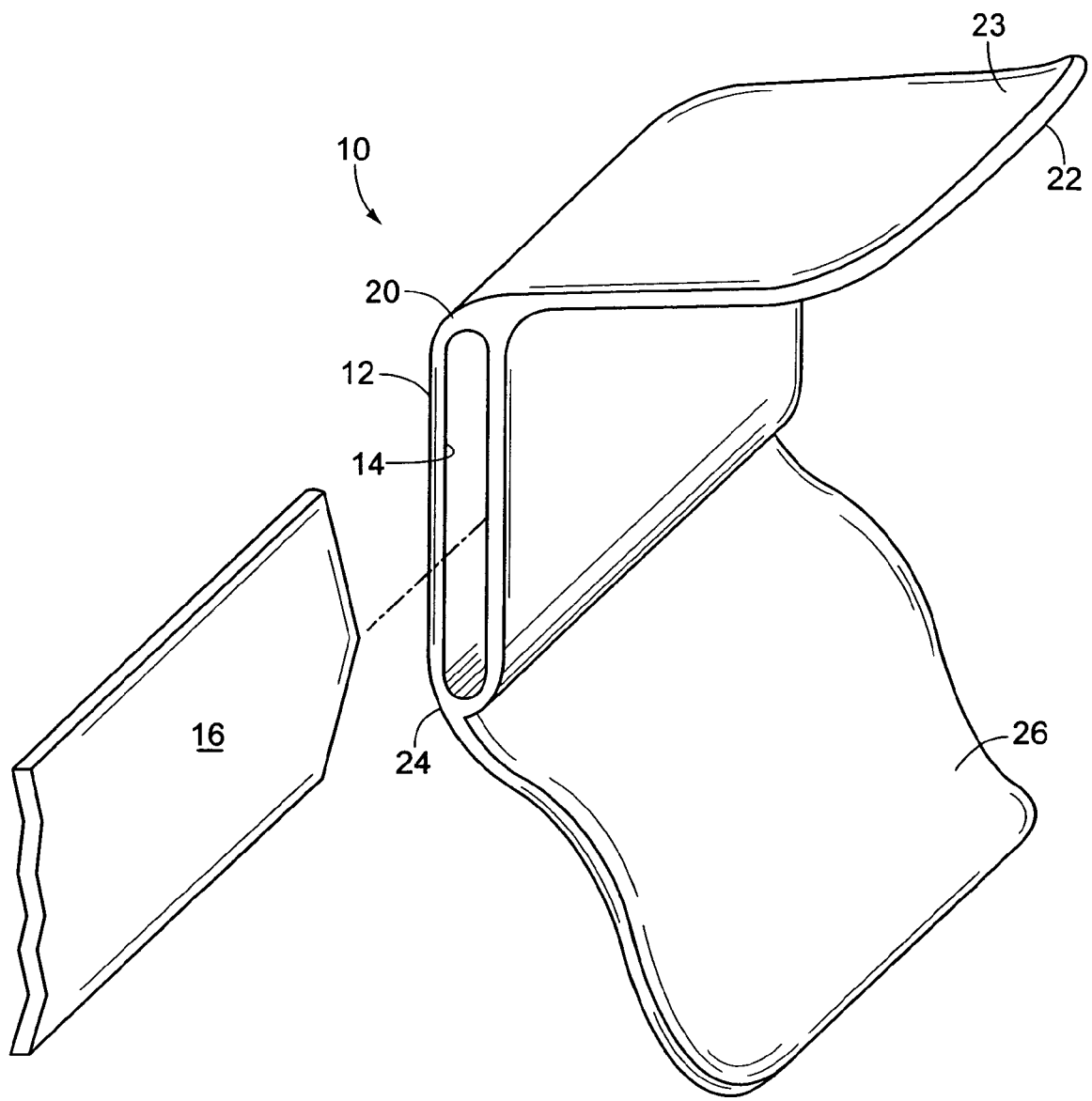
FIG. 1 is a perspective view of a first embodiment body armrest of the present invention illustrated in a right side orientation.

Referring to FIG. 1, there is a perspective view of a first embodiment of the body armrest 10 in a right side orientation. Body armrest 10 in FIG. 1 is of unitary one piece construction and comprises a centrally disposed sleeve 12 defining a passageway 14 therethrough, sleeve 12 and passageway 14 for the slidable receipt through passageway 14 of a waist belt 16. The waist belt 16 may comprise an ordinary pants belt worn by an individual and fashioned through the belt loops of a pair of trousers or pants, or depending upon the wardrobe which the individual is wearing, waist belt 16 may be a web like waist belt worn either against the body's skin or over the clothing worn by the individual. In either embodiment, the waist belt 16 would having a securing means in the front for taut engagement about the waist.

Extending outwardly from the upper portion 20 of sleeve 12 is a platform or arm cradle 22 which has a slightly arcuate surface 23 conforming to the elbow and forearm. Platform or arm cradle 22 provides the support surface when body armrest 10 is secured about the waist of an individual by a waist belt 16. Due to the positioning of the waist belt, the platform or arm cradle 22 is at a height which allows the individual to rest their elbow and forearm 23 on the platform or arm cradle 22. This contact by the elbow and forearm relieves some of the upper body weight which heretofore was supported solely by the spine. Depending arcuately downwardly and outwardly from lower end 24 of sleeve member 14 is a hip contoured leg member 26 which is arcuate and designed to fit the contour of the hip as it emanates from the waist.

The body armrest illustrated in FIG. 1 is illustrated in a right body side configuration, however, the left arm body armrest would be symmetrical and of the same size. The body armrest of FIG. 1 is of unitary construction and can be fabricated rather easily from polymer or other suitable material.

Figure 3:
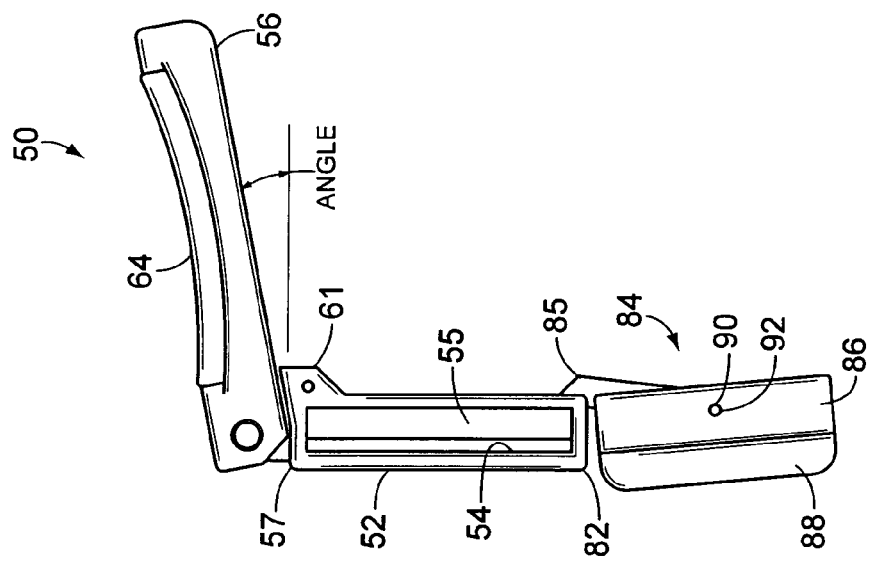
FIG. 3 is an end view of the second embodiment of the body armrest of the present invention when in use.
Figure 2:
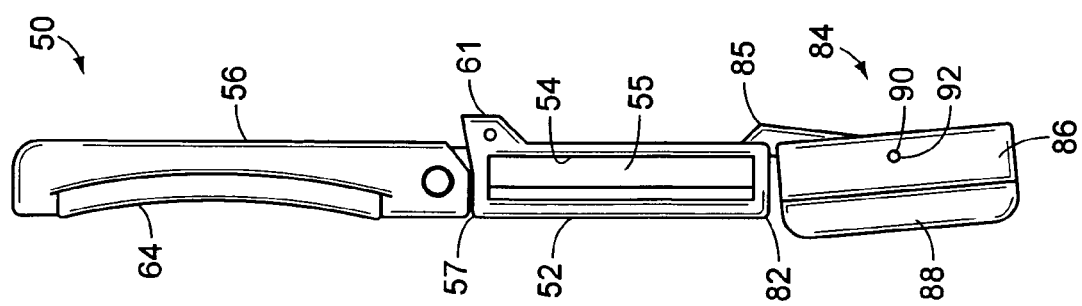
FIG. 2 is an end view of a second embodiment of the body armrest when not in use.
Figure 4:
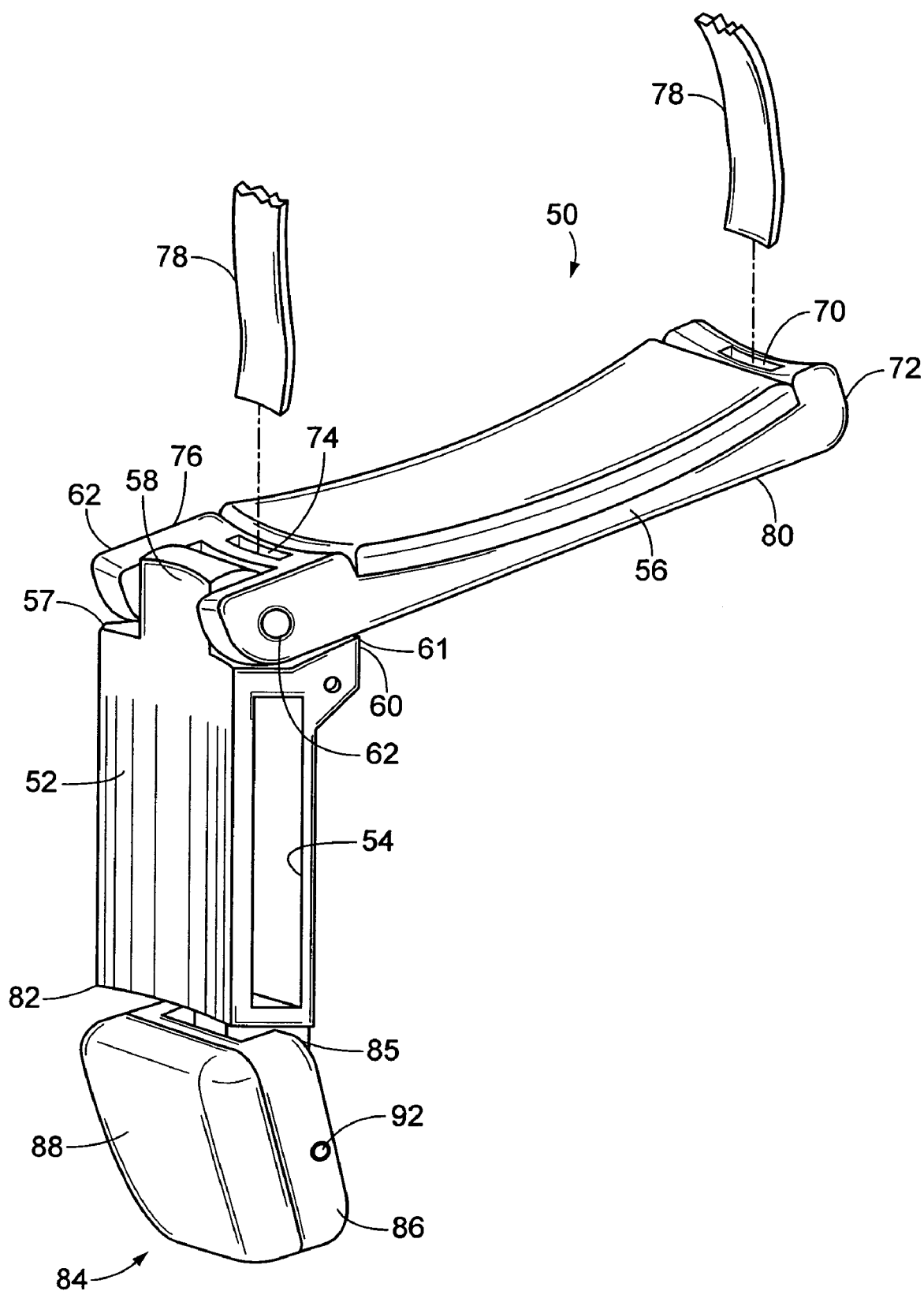
FIG. 4 is a perspective view of the second embodiment of the body armrest.

FIG. 2 is an end view of a second embodiment of the body armrest of the present invention illustrating its positioning when not in use. FIG. 3 is an end view of the second embodiment of the body armrest of the present invention illustrating its positioning when in use. FIG. 4 is a perspective view of the second embodiment of the body armrest. Body armrest 50 serves the same purpose as body armrest 10, that is to allow the wearer and user to rest their elbow and forearm on a supported surface in order to relieve pain and provide for a three point contact for supporting the upper torso. The body armrest 50 comprises a sleeve member 52 having a slot there through 54 so that the body armrest 10 can be affixed to a belt 55 circling the waist of the individual user. The platform or armrest cradle 56 is secured to the upper end 57 of the sleeve member 52. However, in the second embodiment, the platform or armrest cradle 56 is in articulating relationship to the sleeve member 52 there being formed on the upper end 57 of sleeve member 52 a hinge post 58 and platform or armrest cradle 56 is formed with a forked end 60 which would engage on both sides of hinge post 58 and be secured thereto by a pivot pin 62. In this configuration, if the user were wearing the body armrest 50 and did not desire or require their use, the platform or armrest cradle 56 can be rotated upwardly such that it abuts the side or rib cage portion of the individual below the armpit (FIG. 2). When desiring the use of the platform or armrest cradle 56, the wearer merely rotates the platform or armrest cradle 56 to the position illustrated in FIGS. 3 and 4. The sleeve member 52 in the second embodiment incorporates a stop member 61 so as to maintain the platform or armrest cradle in the correct orientation. Still further, optional coil springs (not shown) could be incorporated with the pivot pin 62.

Platform or armrest cradle 56 would be formed of a suitable rigid material, but would have positioned on its upper surface, a resilient flexible pad 64 in order to provide comfort to the user. Still further, the armrest cradle or platform 56 may be formed with a first slot 70 at its extended end 72 and a second slot 74 at its hinged end 76 in order to accommodate an arm strap 78, which arm strap 78 would encircle the lower portion 80 of the platform or armrest cradle 56 and extend over the forearm of the individual or user. Such arm strap 78 may be used when it is desireous of maintaining the individual's arms in contact with the armrest cradle or platform 56.

At the lower end 82 of sleeve member 52 there is positioned an articulating leg 84 designed to engage the curvature of the hip of the individual. Depending leg 84 consists of a base support 86 made of a rigid material overlaid with a resilient padding material 88 which would abut the hip. An arm member 85 rigidly secured to sleeve member 52 and extending downwardly therefrom would have a throughbore 90 there through for receipt of a pivot pin 92 which would extend through the base support 86 and the throughbore of the depending leg member. This would allow the base support 86 and overlaid resilient padding 88 to pivot in relationship to the hip of the individual and thereby allow it to conform to the curvature of the hip for individuals of varying torso configuration. It will further be noted that in the illustration of the second embodiment of the body armrest 50 of the present invention, that the platform or armrest cradle 56 is shown in a user position with a slight angle from the horizontal. This angle is defined by the configuration of the stop member 60 on the sleeve member 52. This is for explanatory purposes only. The stop member 60 may be formed with sleeve member 52 such that the platform or armrest cradle 56 when in a user position is in the horizontal plane or the stop member 60 can be formed such that the platform or armrest cradle is at a slightly angled position.

Figure 5:
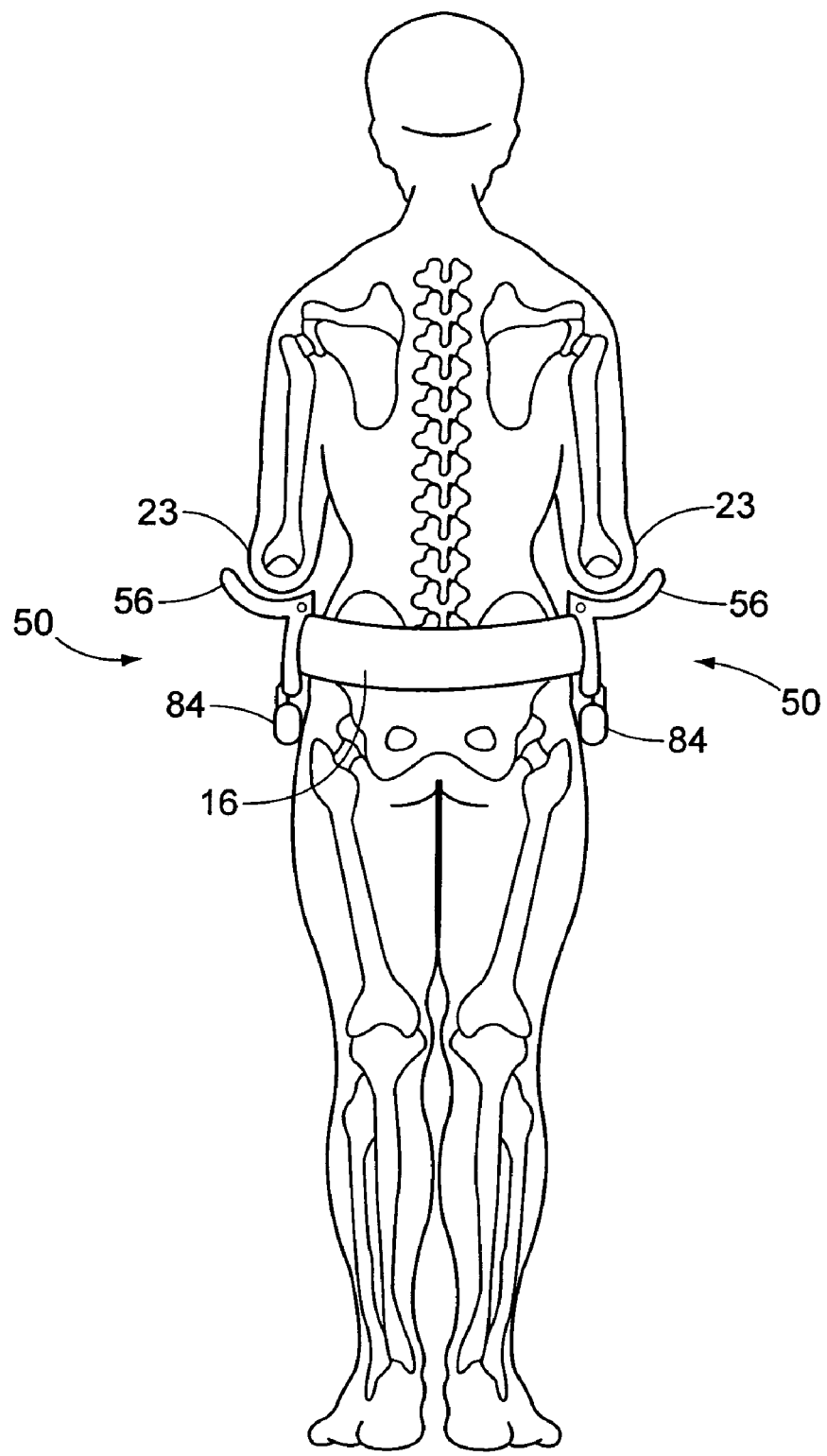
FIG. 5 is a rear view of a human torso with body armrests in position.

FIG. 5 is a rear view of the human body having a waist belt 16 encircling the waist and hips and illustrating a body armrest 50 secured to the waist belt 16 such that the elbow and a portion of the forearm of the individual can rest on the platform or armrest cradle 56. The articulating leg member 84 which depends from sleeve member 52 can articulate in order to conform to the hip curvature of the individual. As stated, the waist belt 16 utilized for the body armrest 50 may be the belt utilized by the user with respect to trousers or pants, or it may be a separate belt which separate belt is used only to secure and maintain the body armrest 50.

In this configuration, the body armrest provides three contact points for the upper torso. The first contact point would be the spine, as is the same with all individuals. However, the body armrest 50 provides two additional contact points for the elbow and a portion of the forearm, the platform or armrest cradle 56 thereby relieving some of the weight heretofore borne solely by the spine. Additionally through the use of the waist belt 16 and the depending arcuately contoured leg member 84, some of the weight borne by the platform or armrest cradle 56 due to the resting of the elbows and a portion of the forearms thereon is transferred to the hips by the body armrest.

The first embodiment of body armrest 10 may be made in varying sizes in order to accommodate different torso configurations and dimensions. Body armrest 10 could also be custom molded to a specific persons torso contours and dimensions. The embodiment illustrated in FIG. 1 could be molded of unitary one piece construction. Still further, the body armrest 10 of the present invention could be molded out of a material which provides some flexibility such that the hip contoured leg member 26 could have some flexion in order to accommodate hip curvature of varying dimensions. Still further, the body armrest 10 of the present invention could be fabricated from light weight metal, such as aluminum, and encapsulated by a resilient flexible material.

While the present invention has been described with respect to the exemplary embodiments thereof, it will be recognized by those of ordinary skill in the art that many modifications or changes can be achieved without departing from the spirit and scope of the invention. Therefore it is manifestly intended that the invention be limited only by the scope of the claims and the equivalence thereof.

We claim:

1. A body armrest worn on the waist of an individual user and supported by a waist belt for support of the elbows and forearms to the user, the body armrest comprising:

a waist belt worn about the waist of the user;

a body armrest secured to said waist belt, one body armrest being positioned on the right waist of the individual and another body armrest positioned on the left waist of the individual, the body armrest having a centrally disposed sleeve member having a passageway therethrough for the receipt of said waist belt, said sleeve member having secured to the upper end thereof, an arm cradle extending outwardly from said sleeve member and said waist of said individual user, said arm cradle positioned at a height so as to permit the individual user to rest the respective right elbow and right forearm on the right side body armrest and the left elbow and left forearm on the left side body armrest;

a depending leg member depending from the lower end of said sleeve member, said depending lower leg member having an arcuate shape designed to conform to an arcuate shape of the hip of the individual and to be in abutting contact with said hip of said individual when said individual user's elbows and forearms are in abutting relationship to said arm cradle.

2. The body armrest in accordance with claim 1 wherein said body armrest is of unitary construction.

3. The body armrest in accordance with claim 1 wherein said depending leg member may be malleable so as to conform to varying hip curvature.

4. The body armrest in accordance with claim 1 wherein said arm cradle may be overlaid with a resilient padding.

5. The body armrest in accordance with claim 1 wherein said arm cradle is in articulating relationship with said sleeve member.

6. The body armrest in accordance with claim 1 wherein said depending leg member is in articulating relationship with said sleep member.

7. A body armrest worn on the waist of an individual user and supported by a waist belt for support of the elbow and forearm of the user, the body armrest comprising:

a waist belt worn about the waist of the user;

a body armrest secured to said waist belt, one body armrest being positioned on the right waist of an individual and another body armrest positioned on the left waist of an individual, the body armrest having a centrally disposed sleeve member having a passageway therethrough for the receipt of said waist belt, said sleeve member having articulating secured to an upper end thereof an arm cradle extending outwardly from said sleeve member and said waist of said individual user, said arm cradle positioned at a height so as to permit said individual user to rest the respective right elbow and right forearm on said right side body armrest and the left elbow and left forearm on said left side body armrest;

a depending leg member articulating secured to a lower end of said sleeve member, said depending lower leg member having an arcuate shape designed to conform to the arcuate shape of the hip of the individual and to be in abutting contact with said hip of said individual when said individual user's elbows and forearms are in abutting relationship to said arm cradle.

8. The body armrest in accordance with claim 7 wherein said arm cradle is formed with a resilient padding thereon.

9. The body armrest in accordance with claim 7 wherein said arm cradle is formed with slotted apertures at opposing ends thereof for receipt of a retaining strap.

10. The body armrest in accordance with claim 7 wherein said articulating depending leg member is overlaid with a resilient padding for abutting contact with said hip.

11. The body armrest in accordance with claim 7 wherein said sleeve member is formed with a stop member to set an angle of said arm cradle when in a extended position.

12. The body armrest in accordance with claim 7 wherein said arm cradle is rotatable to a vertical position in substantial alignment with said sleeve member when not in use.

* * * * *